US006002097A

United States Patent [19]
Morioka et al.

[11] Patent Number: 6,002,097

[45] Date of Patent: Dec. 14, 1999

[54] SYSTEM AND METHOD FOR PRODUCING NEBULIZED SAMPLE ANALYTE CONTAINING SOLUTION FOR INTRODUCTION TO SAMPLE ANALYSIS SYSTEMS

[75] Inventors: Akihiro Morioka, Chiba Prefecture; Junichi Takahashi; Toshikazu Amano, both of Tokyo, all of Japan; William J. Stein, Council Bluffs, Iowa; Robert C. Fry, Omaha, Nebr.

[73] Assignees: Transgenomic, Inc., San Jose, Calif.; Yokogawa Analytical Systems, Inc., Tokyo, Japan

[21] Appl. No.: 09/144,893

[22] Filed: Sep. 1, 1998

[51] Int. Cl.[6] .................................................. B23K 9/00

[52] U.S. Cl. .............................. 219/121.52; 219/121.59; 315/111.51

[58] Field of Search ......................... 219/121.52, 121.59; 250/288; 356/246; 315/111.21, 111.51

[56] References Cited

U.S. PATENT DOCUMENTS

| | | | |
|---|---|---|---|
| 4,517,495 | 5/1985 | Piepmeier | 315/111.21 |
| 4,575,609 | 3/1986 | Fassel et al. | 219/121.59 |
| 4,926,021 | 5/1990 | Streusand et al. | 219/121.59 |
| 4,990,740 | 2/1991 | Meyer | 219/121.52 |
| 5,192,865 | 3/1993 | Zhu | 250/288 |
| 5,212,365 | 5/1993 | Weiderin | 219/121.52 |
| 5,229,605 | 7/1993 | Bridenne et al. | 250/282 |
| 5,233,156 | 8/1993 | Chan | 219/121.52 |
| 5,259,254 | 11/1993 | Zhu | 73/864.81 |
| 5,272,308 | 12/1993 | Wiederin | 219/121.52 |
| 5,381,008 | 1/1995 | Tanner et al. | 250/288 |
| 5,867,262 | 2/1999 | Etoh et al. | 356/246 |

OTHER PUBLICATIONS

Cetac MCN–100 Microconcentric Nebulizer Product Sheet.
Hewlett Packard HP4500 ICP–MS Product Sheet.

*Primary Examiner*—Mark Paschall
*Assistant Examiner*—Quang Van
*Attorney, Agent, or Firm*—James D. Welch

[57] ABSTRACT

The present invention is a system for nebulizing sample analyte containing solutions which allows liquid solution and gas entry, and is tyically utilized in combination or integration with an interface for directing sample analyte containing solution which is nebulized. The present invention provides improvement in the form of system design that prevents sample delivery tube component damage, sample solution electrical charging, sample solution "re-nebulization" effects, and sample analyte carry-over memory effects during a present invention method of use for introducing nebulized sample analyte containing solution into, for instance, a mass-spectrometer sample analysis system.

28 Claims, 5 Drawing Sheets

SYSTEM AND METHOD FOR PRODUCING NEBULIZED SAMPLE ANALYTE CONTAINING SOLUTION FOR INTRODUCTION TO SAMPLE ANALYSIS SYSTEMS

TECHNICAL FIELD

The present invention relates to systems used in nebulizing sample analyte containing solutions, said systems presenting with liquid solution, and gas, entry means. More particularly the present invention comprises systems for nebulizing sample analyte containing solutions which include means for preventing sample delivery tube damage, means for preventing sample solution electrical charging, means for preventing sample solution "re-nebulization" effects and means for preventing sample analyte carry-over memory effects during a present invention method of use for introducing nebulized sample analyte containing solution into sample analysis systems such as mass-spectrometer systems.

BACKGROUND

The sample analyte analysis capabilities of Inductively Coupled Plasma-Mass Spectrometer (ICP-MS) and Microwave Coupled Plasma-Mass Spectrometer (uW-MS) systems and the like, are well established.

For insight, it is noted that (ICP-MS) systems can comprise an Inductively Coupled Plasma (ICP) system followed by a Mass-Spectrometer (MS) system, wherein the (ICP) system is an (ICP) "Torch" with an enclosed space therein in which a plasma is inductively formed by application of high frequency electrical energy, via a coil situated around said enclosed space. An (ICP) Torch, it is mentioned, typically comprises a "Sample Injector Tube" present centrally within various other concentrically surrounding tubes, which various other concentrically surrounding tubes typically project beyond the projecting end of said sample injector tube, thereby providing an enclosed space therewithin, beyond the projecting end of said sample injector tube. Typically, during use, a sample solution is distally nebulized, (ie. atomized into small diameter droplets), and the nebulized droplets are caused to flow through said sample delivery tube into said plasma containing enclosed space. Gas is simultaneously caused to flow through annular space(s) between concentric tubes within said (ICP) Torch with the effect being that nebulized sample is directed into the plasma containing enclosed space in a plume. When a sample component is injected into said plasma containing enclosed space of an (ICP) Torch, electrons therein are excited into high energy atomic orbitals and some are dislodged entirely, thereby providing ionized sample components which are suitable for analysis in a mass-spectrometer system.

Other sample analyte ionization system configurations eliminate the need for an (ICP) Torch and provide for ionization of nebulized sample analyte injected thereinto by functionally equivalent means. For instance, entry stage ionization chambers contained within a Mass-Spectrometer (MS) system are such functionally equivalent means.

It is to be understood that Mass-Spectrometer (MS) systems comprise means for identifying ionized, (charged), sample components, (ie. analytes), based upon their mass and charge, as mediated and evidenced by said ionized charged sample component trajectory in the presence of electric and/or magnetic fields. For instance, which detector, (in an array of detectors oriented so as to intercept charged particles), a charged particle of a certain mass and charge which is caused to move in an electric field, enters, is determined by factors including the strength of the electric field, the particle velocity, charge and mass.

To provide additional insight it is disclosed that known means for nebulizing sample analyte containing sample solution, prior to injection into an (ICP), include Direct Injection Micronebulizer (DIN) systems. Briefly, (DIN) systems are well suited for directly entering small volumes of nebulized sample analyte containing solution into a plasma, and comprise a sample delivery tube centrally present within an essentially elongated tubular space through a "primary body element", such that during use sample analyte containing solution can be caused to eject from an end of said sample delivery tube simultaneous with the ejecting of a gas from an annular space concentrically formed between an outer surface of said sample delivery tube, and an inner surface of the elongated tubular space through said primary body element. Interaction between said ejecting sample analyte containing solution and said ejecting gas causes said sample analyte containing solution to become subjected to shearing forces and thereby nebulized into small droplets. Preferred (DIN) systems produced by CETAC/TRANSGENOMIC Inc. (which is headquartered in Omaha, Neb., and which is the Assignee for all Wiederin and Zhu Patents cited herein), typically include means for adjusting the positioning of an end of a sample delivery tube with respect to the end of the concentrically surrounding primary body element. Said positioning, it is noted, is often critical to successful nebulization of entered sample analyte containing solution.

Additional known systems for nebulizing sample analyte containing sample solution are known as Micro-Concentric Nebulizer Systems, (eg. MCN systems), and while (MCN) systems are generally functionally similar to (DIN) systems, (MCN's) are often simpler in that they comprise a primary body element with provision for simultaneous entry of both sample analyte containing sample solution and a flow of gas, and with provision for securing to a Spray Chamber which is sequentially present prior to a an Inductively Coupled Plasma (ICP) or Mass-Spectrometer (MS) system. That is, (MCN) systems need not be of a shape and size such that they can be easily inserted into an (ICP) Torch, and need not provide means for enabling the positioning of a sample solution ejecting end thereof near to an (ICP) in use. Instead, an (MCN) system need provide only means for simultaneous entry of sample analyte containing sample solution and a flow of gas, and means for coupling to a sequentially next stage, (eg. a spray chamber).

A Search of relevant references has identified a Fassel et al. U.S. Pat. No. 4,575,609 which describes a micronebulizer which inserts in, and mounts directly to a sample injector tube of a standard (ICP) torch. U.S. Pat. Nos. 5,212,365 and 5,272,308 to Wiederin describe improved (DIN) systems which do not require the presence of an (ICP) Torch sample injector tube as a part of their construction, but rather provide an elongated primary body element with a longitudinally oriented hole therethrough, through which longitudinally oriented hole a centrally located sample delivery tube extends. The Wiederin (DIN) systems allows for easy access to the space inside the Primary Body Element to allow non-destructive cleaning, and allows easy adjustment of the location of the relative positions of the sample ejecting end of the Sample Delivery Tube and the end of the Primary Body Element. Said adjustment allows optimizing the nebulizing ability of the Wiederin (DIN). A Meyer U.S. Pat. No. 4,990,740 describes a low operational pressure (DIN)-like system at a lower aspect thereof, with a series of impactors thereabove. Said impactors serve to deflect large diameter droplets, (over approximately fifteen (15) microns in diameter), away from injection into an upper aspect of said system.

A Chan et al. U.S. Pat. No. 5,233,156 is also known and teaches Torches of the type used in (ICP) systems, which Torches are designed for use with high solids content samples. Standard (ICP) torches are also described therein.

Another known U.S. Pat. No. 5,192,865 to Zhu is also disclosed as it describes entry of a nebulized sample analyte into a (MS) system via an Atmospheric Pressure Afterglow Ionization System. Nebulized sample analyte is injected into said 865 Patent system sequentially after the location of a carrier gas ionization means which serves to produce metastable species in use. In addition, another known Zhu U.S. Pat. No. 5,259,254 is also disclosed as it describes nebulization of a sample analyte containing solution, (by ultrasonic means), in a system which comprises a spray-chamber.

As mentioned, in some applications of sample solution nebulizing systems, it is not necessary to position an end of the sample solution nebulizing system from which nebulized sample solution is caused to exit in use, near a plasma in, for instance, an (ICP) system. The 308 Patent to Wiederin et al. describes such a system wherein is present, (between a (DIN) and a (MS) system), sequentially intervening desolvation and enclosed filter solvent removal systems, the purpose thereof being to remove and dispose of solvent in nebulized sample analyte containing sample solution droplets prior to entry of desolvated nebulized sample analyte to said (MS) system.

Importantly, it has been noted that in certain applications of (DIN) and (MCN) systems, at times sample solution delivery tubes, (ie. tubes which carry sample analyte containing sample solution), become crushed, thereby blocking flow of sample analyte containing solution therethrough. This is especially true where a utility providing thin-walled capillary is utilized as sample delivery tube. It has also been noted that flow of sample analyte containing solution through (DIN) or (MCN) systems can, during use, cause sample analyte containing solution therein to become electrically charged. Discharge of said electrical charge has been noted to induce untoward spikes in (MS) system output, thereby reducing sample analyte analysis capability. In addition, where a (DIN) or (MCN) is secured to a spray chamber means, it has been found that relatively large droplets of nebulized sample analyte containing solution can condense therein, onto the end of the (DIN) or (MCN) from which exits nebulized sample analyte containing solution in use. This can interrupt smooth flow of nebulized sample analyte containing solution, and can result in an undesirable effective “re-nebulization” of said condensed sample analyte containing solution, by gas exiting the (DIN) or (MCN). This effect is undesirable as it complicates interpretation of results provided by use of a (MS) system into which resulting nebulized sample solution is entered. It is also noted that systems for nebulizing, and analyzing, analytes in sample analyte containing solutions which have crevasses therein are prone to sample analyte carry-over “memory effects”, wherein sample analyte entered during one analysis procedure is retained and undesirably released during a subsequent sample analysis procedure. Said “memory effect” is undesirable as it can lead to erroneous indication of the presence of a sample analyte in a specific sample analyte containing solution in which it is not actually present.

It should then be appreciated that even in view of the identified known art, need remains for convenient-to-use systems which include a relatively physically simple, (eg. MCN), system for subjecting a sample analyte containing solution to a nebulization procedure, followed by injection of the results into an (ICP), or functionally equivalent sample analyte ionization system, wherein ionization of sample analyte analytes occurs in use, so that a sequentially following (MS) system can be applied to the detection, and analysis, of sample analyte(s) present therein. Said relatively simple system for subjecting a sample analyte containing solution to a nebulization procedure, should provide for use with spray-chamber and/or desolvation means and/or solvent removal means, between it and a sample analysis system such as an (MS) system without introducing identified difficulties associated with sample delivery tube kinking and/or crushing at points of securement to said sample analyte containing solution nebulizing means, electrostatic spike development, the occurrence of sample solution “re-nebulization” and sample analyte memory effects, in addition to providing function enhancing interface system means for interconnecting said relatively simple system for subjecting a sample analyte containing solution to a nebulization procedure, to a spray-chamber and/or desolvation means and/or solvent removal system means.

DISCLOSURE OF THE INVENTION

The present invention is a system for use in preparing a sample analyte containing solution for introduction into a sample analysis system.

One embodiment of the present invention system comprises a sample delivery tube for carrying sample analyte containing sample solution; a nebulizer means comprising a primary body element which contains a through-hole, (eq. a micro-concentric nebulizer); a means for receiving nebulized sample analyte containing sample solution, (eg. a spray chamber); and an interface means which comprises means for receiving said nebulizer means at a first side thereof and a means for receiving said means for receiving nebulized sample analyte containing sample solution at a second side thereof.

Said sample delivery tube for carrying sample analyte containing sample solution is secured into said through-hole of said nebulizer means, and said nebulizer means is secured into said interface means at said means for receiving said nebulizer means present at said first side of said interface means. In addition, said means for receiving nebulized sample analyte containing sample solution is secured into said interface means at said means for receiving said means for receiving nebulized sample analyte containing sample solution at said second side of said interface means. It is noted that both said means for receiving said nebulizer means and said means for receiving nebulized sample analyte containing sample solution are preferably essentially cylindrically shaped bores, (optionally comprising female threading), in said interface means, and typically the means for receiving said nebulizer means bore is of a smaller diameter than the means for receiving nebulized sample analyte containing sample solution bore.

In use, sample analyte containing solution is caused to flow through said sample delivery tube, enter said nebulizer means wherein it becomes nebulized, and resulting nebulized sample analyte containing solution is then injected into said means for receiving nebulized sample analyte containing sample solution.

Prior art systems which contain elements as just described have been found to be prone to various operational difficulties, and said present invention system is distinguished in that at least one operational difficulty selected from the group consisting of:

a. sample delivery tube kinking and/or crushing at a point of securement to said nebulizer system;

b. electrostatic spike development resulting from the flow of sample analyte through said sample delivery tube and nebulizer means;

c. the occurrence of sample solution "re-nebulization", where nebulized sample analyte containing solution which is injected into said means for receiving nebulized sample analyte containing sample solution condenses, and flows over an exit means, (eg. nozzle) of said nebulizer means; and d. the occurrence of sample analyte retention, from one sample analysis procedure to another, in gaps or crevasses.

is/are substantially overcome.

The problem of sample delivery tube kinking and/or crushing at a point of securement to said nebulizer system is overcome by providing at least two circumscribing protective concentric tubing layers around said sample delivery tube at a location thereof where said sample delivery tube is secured in said through-hole of said nebulizer means, said at least two protective layers serving to prevent sample delivery tube kinking and/or crushing in use resulting from securing effected forces. Preferred circumscribing protective concentric tubing layers are made of at least one material selected from the group consisting of: (a fluorocarbon, PTFE, PFA, a polyimide, a metal, a ceramic, stainless steel, a rigid plastic, and PEEK), and said sample delivery tube is secured in said through-hole of said nebulizer means by a ferrule. A preferred sequence of protective layers provides that three such layers be present and is:

a. said sample delivery tube;

b. a first circumscribing layer of heat shrinkable material;

c. a second circumscribing layer of strength providing material such as metal or ceramic; and d. a third circumscribing layer of heat shrinkable material.

The problem of preventing electrostatic spike development, (which results from sample analyte flow inside a present invention sample delivery tube or nebulizer means etc.), is overcome by fabricating at least one selection from the group consisting of: (an element of said nebulizer means and said sample delivery tube), with which sample analyte containing solution makes contact in use, from an electrically conductive material, which electrically conductive material is, in use, connected to a charge draining "ground". Where the nebulizer means is made from an electrically conductive material said sample delivery tube is fabricated to be other than totally confining of sample analyte containing solution entered thereinto. This allows sample analyte containing solution entered thereinto, access to said electrically conductive material, to the end that sample analyte containing solution caused to enter said nebulizer means, in use, makes direct contact electrical with said electrically conductive material. It is noted that a preferred electrically conductive material is graphite impregnated PEEK.

The problem of sample solution "re-nebulization" is overcome by providing an element selected from the group consisting of: (said nebulizer means and said interface means), with an exit means for injecting sample analyte containing solution which has been nebulized into said means for receiving nebulized sample analyte containing sample solution, which exit means comprises a bottle-neck shape wherein a relatively small diameter portion is bounded by two relatively larger diameter portions. In use nebulized sample analyte containing solution which condenses in said means for receiving nebulized sample analyte containing sample solution is caused, (by the present invention bottle-neck design), to be far less likely to flow over the exit means for injecting sample analyte containing solution which has been nebulized, and thereby be subject to "re-nebulization" at said exit, (eg. nozzle), point.

The problem of sample analyte retention from one analysis procedure to another is overcome by present invention system design which eliminate gaps or crevasses between interconnected elements.

A present invention system can include all identified means for overcoming all identified problems, (ie. sample delivery tube kinking and/or crushing and electrostatic spike development and the occurrence of sample solution "re-nebulization" and retention of sample analyte between analysis procedures), or any one or two or three thereof.

A modified embodiment of the present invention system for use in preparing a sample analyte containing solution for introduction into a sample analysis system provides that the nebulizer means and the interface means be considered as functionally integrated. Said modified embodiment then comprises a sample delivery tube for carrying sample analyte containing sample solution, said sample delivery tube having a tubular wall with at least one attribute selected from the group consisting of: (having no opening or discontinuity therein, having at least one opening therein and having at least one discontinuity therein). Said modified embodiment further comprises a combination nebulizer means and interface means which presents with a through-hole and means for receiving a means for receiving nebulized sample analyte containing sample solution. Said sample delivery tube for carrying sample analyte containing sample solution is secured into said through-hole of said combination nebulizer means and interface means, and said combination nebulizer means and interface means is preferably at least partially made of an electrically conductive material, to which electrically conductive material sample analyte containing solution entered via said sample delivery tube makes electrical contact in use via an opening or discontinuity therein. An alternative embodiment provides for the sample delivery tube which has no hole or discontinuity therein, to be made of an electrically conductive material. In either case the electrically conductive material is connected to a charge draining "ground", with the result being that electrostatic spike development resulting from the flow of sample analyte containing solution during operation is substantially eliminated.

As for the first described embodiment of the present invention, said modified embodiment of the present invention system for use in preparing a sample analyte containing solution for introduction into a sample analysis system can also further comprises at least two circumscribing protective concentric tubing layers around said sample delivery tube at a location thereof where said sample delivery tube is secured in said through-hole of said combination nebulizer means and interface means, said at least two protective layers serving to prevent sample delivery tube kinking and/or crushing, and again said securing effected forces are typically developed by sample delivery tube securing ferrules present in said through-hole in said functionally integrated nebulizer means and interface means. Again, as described infra herein, a preferred sample delivery tube comprises circumscribing protective concentric tubing layers which are made of at least one material selected from the group consisting of: (a fluorocarbon, PTFE, PFA, a polyimide, a metal, a ceramic, stainless steel, a rigid plastic, and PEEK), and said sample delivery tube is secured in said through-hole of said nebulizer means by a ferrule. Again, a preferred sequence of protective layers is:

a. said sample delivery tube;

b. a first circumscribing layer of heat shrinkable material;

c. a second circumscribing layer of strength providing material such as metal or ceramic; and d. a third circumscribing layer of heat shrinkable material.

Any embodiment of the present invention system for use in preparing a sample analyte containing solution for introduction into a sample analysis system typically also further sequentially comprises an inductively coupled plasma (ICP) or functionally equivalent sample analyte ionization system, (eg. microwave induced plasma (uIP) or an input stage of a Mass Spectrometer), which is functionally attached to said means for receiving nebulized sample analyte containing sample solution, (eg. spray chamber). In said inductively coupled plasma (ICP) or functionally equivalent sample analyte ionization system, ionization of sample analyte(s) occurs in use to the end that said mass spectrometer (MS) system can be applied to the detection, and analysis, of sample analyte(s) present therein.

It Is also noted that any present invention system for use in preparing a sample analyte containing solution for introduction into a sample analysis system also further comprises a means for entering a sample analyte containing solution nebulizing flow of carrier gas in at least one selection from the group consisting of: (said nebulizer means and said interface means and an integrated nebulizer means/interface means). It should be appreciated that in a micro-concentric nebulizer it is shear force interaction between a flow of sample analyte containing solution and a flow of entered carrier gas the leads to sample analyte containing solution nebulization.

Additionally, said means for receiving nebulized sample analyte containing sample solution also typically contains a drain means to allow exit of relatively large droplets which result from a nebulization process and which fall under gravity, rather than being carried by the flow of entered carrier gas to an ionization system.

In one embodiment, the interface means for receiving said nebulizer means at a first side thereof and means for receiving said means for receiving nebulized sample analyte containing sample solution at a second side thereof are each an essentially tubular threaded female hole, said nebulizer means primary body element and means for receiving nebulized sample analyte containing sample solution each have complimentary mating threaded male shafts. In use said nebulizer means primary body element is affixed to said interface means for receiving said nebulizer means at said first side thereof by being screwed thereinto, and such that said means for receiving nebulized sample analyte containing sample solution is affixed to said interface means for receiving said nebulizer means at said second side thereof by being screwed thereinto. It is noted, however, that it is within the scope of the present invention to mount nebulizer means and/or means for receiving nebulized sample analyte containing sample solution to an interface means by use of "O" rings.

An alternative description of a present invention sample introduction system provides that a nebulizer means comprising means for simultaneously introducing sample analyte containing solution, and a flow of carrier gas, to the end that said sample analyte containing solution is nebulized therein into droplets of varying sizes be present, in addition to a spray chamber means capable of condensing relatively large diameter droplets and expelling them therefrom, and an interface means having a through-hole comprising a first diameter side and a second diameter side, said nebulizer means being engaged in said first diameter side and said spray chamber means being engaged in said second diameter side. A sample delivery tube for use in providing sample analyte containing solution into said nebulizer means is also present and is secured in said through-hole of said nebulizer means by way of ferrule means. Said interface means for receiving said nebulizer means at a first side thereof and means for receiving said means for receiving nebulized sample analyte containing sample solution at a second side thereof are each an essentially tubular threaded female hole, and said nebulizer means primary body element and means for receiving nebulized sample analyte containing sample solution each have complimentary mating threaded male shafts; such that in use said nebulizer means primary body element is affixed to said interface means for receiving said nebulizer means at said first side thereof by being screwed thereinto, and such that said means for receiving nebulized sample analyte containing sample solution is affixed to said interface means for receiving said nebulizer means at said second side thereof by being screwed thereinto. As described infra herein with respect to other embodiments, said sample introduction system preferably further comprises at least two circumscribing protective concentric tubing layers around said sample delivery tube at the location thereof where said sample delivery tube is secured in said through-hole of said nebulizer means by way of said ferrule means, said at least two protective layers serving to prevent sample delivery tube kinking and/or crushing. Said sample introduction system also preferably further comprises an element selected from the group consisting of: (said nebulizer means and said interface means), which provides an exit means for injecting sample analyte containing solution which has been nebulized by said nebulizer means, into said means for receiving nebulized sample analyte containing sample solution, said exit means having a bottle-neck shape wherein a relatively small diameter portion is bounded by two relatively larger diameter portions. A portion of said means for injecting sample analyte containing solution which has been nebulized by said nebulizer means beyond said bottle-neck shape can be termed a "nozzle". In use nebulized sample analyte containing solution which enters to and condenses in said means for receiving nebulized sample analyte containing sample solution, is less likely to flow over the nozzle region of said exit means for injecting sample analyte containing solution into said means for receiving nebulized sample analyte containing sample solution, and thereby be subject to "re-nebulization" at said nozzle. Said sample introduction system sample delivery tube can be discontinuous within said through-hole within said nebulizer means, and at least one selection from the group consisting of: (an element of said nebulizer means and said sample delivery tube), with which sample analyte containing solution makes contact in use, is made of an electrically conductive material, which, in use, is connected to a charge draining "ground", so as to prevent electrostatic spike development, caused by the flow of sample analyte through said sample delivery tube and/or nebulizer means etc.

Another alternative description provides that a present invention system for use in preparing a sample analyte containing solution for introduction into a sample analysis system be comprised of an interface means for receiving a first element at a first side thereof and means for receiving a second element at a second side thereof. Said means for receiving a first element and means for receiving a second element are separated by a barrier in said interface means which has a barrier through-hole therein which interconnects said means for receiving a first element at said first side thereof and means for receiving a second element at said second side thereof, and each of said means for receiving a first element and means for receiving a second element being an essentially tubular threaded female hole. Said first element and second element are each a threaded male shaft; such that in use said first element is affixed to said interface receiving means by being screwed thereinto, and such that said second element is affixed to said interface means for receiving said nebulizer means at said second side thereof by being screwed thereinto. Each of said first and second elements have through-holes into each of which is secured a sample delivery tube segment. Each of said first and second element through-holes has an into-the-element projecting tapering shape region near the end thereof which becomes positioned adjacent to said barrier when said first and second elements are screwed into said interface means, and said tapering shape region shape is appropriate for receiving a ferrule which is slide over the sample delivery tube segment present in the element which affixes to the means for receiving an element adjacent to said tapering shape region. Said barrier, on at least on side thereof, has a tapering shape region near said barrier through-hole, said tapering shape region being appropriate for receiving a ferrule which slides over the sample delivery tube segment present in the first and/or second element which affixes to said interface means at said at least one side of said barrier. When each said first and second elements have sample delivery tube segments present in through-holes therein, and when ferrules are slid over the sample delivery tube segments at ends thereof, which ends will be positioned adjacent to said barrier in use, and when said first and second elements are screwed into said interface element, said furrules are partially collapsed by adjacent tapering shape regions, thereby securing said sample delivery tube segment. Said interface means further comprise, at one side thereof, a sample delivery tube segment containing exit means which, in use, receives sample analyte containing solution through said barrier through-hole and adjacent sample delivery tube segment, said exit means having a bottle-neck shape wherein a relatively small diameter portion is bounded by two relatively larger diameter portions, a portion of said interface means beyond said bottle-neck shape being a nozzle region. The purpose of said bottle-neck shape is to cause nebulized sample analyte containing solution which exits said nozzle region as nebulized sample analyte containing solution and then condenses, to be less likely to flow over the nozzle region of said exit means become "re-nebulized" by carrier gas exiting at said nozzle. Said interface means further comprises means for entering a sample analyte containing solution nebulizing flow of carrier gas into an annular space around the outer surface of the sample delivery tube segment which provides sample analyte containing solution to nozzle region, such that carrier gas and sample analyte containing solution simultaneously exit at said nozzle and interact to the end that said sample analyte containing solution becomes nebulized. In use sample analyte containing solution is entered to the sample delivery tube segment present at the side of the interface means which does not have the exit means present, such that said ample analyte containing solution flows through said barrier through-hole, into the sample delivery tube segment at the side of the interface means which has the exit means present, and such that a flow of carrier gas is entered to said means for entering a sample analyte containing solution nebulizing flow of carrier gas. The result is that entered sample analyte containing solution is nebulized into a multiplicity of nebulized droplets.

In any embodiment of the present invention sample introduction system said nebulizer means primary body element can be affixed to said interface means for receiving said nebulizer means at said first side thereof by being screwed thereinto in a manner such that no gaps or crevasses are present between said nebulizer means primary body element and said interface means.

In addition, said interface means for receiving said nebulizer means at said first side thereof and said means for receiving said means for receiving nebulized sample analyte containing sample solution at said second side thereof communicate to one another via a relatively small diameter barrier through-hole therebetween, with the transition between said relatively small diameter hole and said means for receiving nebulized sample analyte containing sample solution at said second side of said interface means being cone shaped. An integrated nebulizer means-interface system can also have said cone shaped region present. In use said cone shaped region is positioned around an exit means of a nebulizer means or integrated nebulizer means and interface means. The purpose of said cone shaped region being to direct nebulized sample analyte containing solution which condenses in a means for receiving nebulized sample analyte containing solution, into a bottle-neck shape relatively small diameter portion, (which is bounded by two relatively larger diameter portions), of a nebulized sample analyte containing solution exit means, so that said condensate does not present at a location on said exit means, (eg. a nozzle), such that it is "re-nebulized".

The present invention will be better understood by reference to the Detailed Description Section of this Disclosure, in conjunction with the Drawings.

SUMMARY OF THE INVENTION

It is therefore a purpose of the present invention to provide a convenient-to-use system for use in subjecting a sample analyte containing solution to a nebulization procedure, (such as a microconcentric nebulizer (MCN)), in which system operational difficulties associated with sample delivery tube kinking and crushing, electrostatic spike development and the occurrence of sample solution "re-nebulization" are substantially overcome.

It is another purpose of the present invention to describe an interface means for use in coupling said convenient-to-use system for use in subjecting a sample analyte containing solution to a nebulization procedure, such as a microconcentric nebulizer (MCN), to, for instance, a spray chamber.

It is yet another purpose of the present invention to provide an integrated combination of:

a. a convenient-to-use system for use in subjecting a sample analyte containing solution to a nebulization procedure, (such as a microconcentric nebulizer (MCN)), in which system operational difficulties associated with sample delivery tube kinking or crushing, electrostatic spike development and the occurrence of sample solution "re-nebulization" are substantially overcome; and b. an interface means for use in coupling said convenient-to-use system for use in subjecting a sample analyte containing solution to a nebulization procedure, such as a microconcentric nebulizer (MCN), to, for instance, a spray chamber.

It is another purpose yet of the present invention to describe the presence of a spray-chamber, (optionally in combination with desolvation means and/or solvent removal means), attached to a interface means, such that in use said convenient-to-use system for use in subjecting a sample analyte containing solution to a nebulization procedure, (such as a microconcentric nebulizer (MCN)), enters nebulized sample analyte containing solution droplets thereinto via said interface means.

It is a further purpose of the present invention to describe injection of nebulized sample exiting from a spray-chamber into an (ICP), or functionally equivalent sample analyte ionization system, wherein ionization of sample analyte(s) occurs in use, so that a sequentially following (MS) system can be applied to the detection, and analysis, of sample analyte(s) present therein.

It is another purpose of the present invention to teach that kinking and crushing of a sample delivery tube is conveniently prevented by applying various protective concentric tubing layers thereto at locations where kinking or crushing can otherwise occur, including positions inside said convenient-to-use system for use in subjecting a sample analyte containing solution to a nebulization procedure, (such as a microconcentric nebulizer (MCN)), where ferrules are used to secure a sample delivery tube in place.

It is another purpose yet of the present invention to describe that electrostatic spike development, resulting from the flow motion of sample analyte containing solution through a sample delivery tube in a convenient-to-use system for use in subjecting a sample analyte containing solution to a nebulization procedure, (such as a microconcentric nebulizer (MCN)), can be prevented by causing flowing sample analyte containing solution to come into contact with an electrically conductive element, which is connected to a charge draining "ground".

It is yet still another purpose of the present invention to describe that an element of a convenient-to-use system for use in subjecting a sample analyte containing solution to a nebulization procedure, (such as a microconcentric nebulizer (MCN)), can be made of an electrically conductive material, (such as graphite impregnated PEEK), and serve as an electrically conductive element which is connected to charge draining "ground" so as to prevent electrostatic spike development where system design provides for contact to said sample analyte containing solution in use.

It is still another purpose of the present invention to describe that the occurrence of condensed sample solution "re-nebulization" at the exit point, (ie. nozzle), of a convenient-to-use system for use in subjecting a sample analyte containing solution to a nebulization procedure, (such as a microconcentric nebulizer (MCN)), can be essentially eliminated by providing a bottle-neck configuring just prior to said exit point.

DETAILED DESCRIPTION

Figure 1:
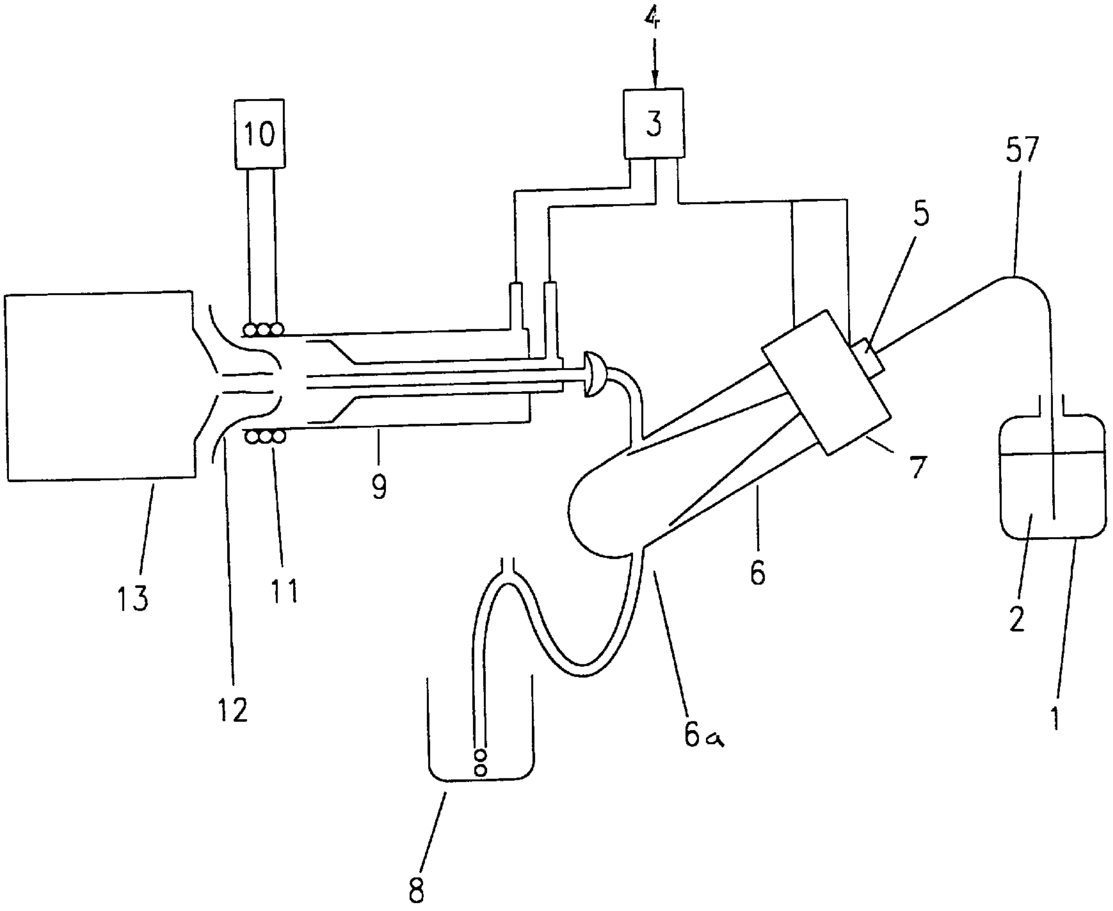
FIG. 1 shows an overall system for producing nebulized sample analyte containing solution and for interfacing nebulized sample analyte containing solution to a sample analysis system.

Turning now to the Drawings, there is shown in FIG. 1 an overall system for producing nebulized sample analyte containing solution and for interfacing nebulized sample analyte containing solution to a sample analysis system, (eg. a mass spectrometer system) (13).

Shown in FIG. 1 are:

a. a source (1) of sample analyte containing solution (2);

b. a sample delivery tube (57) which serves to provide sample analyte containing solution (2) to c. a system for producing nebulized sample analyte containing solution (ie. a nebulizer means) (5), d. an interfacing means (7) for interfacing to e. means for receiving nebulized sample analyte containing solution (eg. a spray chamber (6) which includes a drain means **(6*a*)**);

f. a means for ionizing sample analyte(s), (eg. an inductively coupled plasma (ICP) torch system) (9), including a plasma inducing electromagnetic coil (11). (It is to be understood that microwave or other sample analyte ionization means can be present in place of the shown plasma torch (9) and plasma inducing electromagnetic coil (11), and it is noted that some mass spectrometer sample analysis systems (13) provide an input stage ionization chamber thereby negating the need for additional ionization means such as the plasma torch (9). The FIG. 1 shown plasma torch (9) and plasma inducing electromagnetic coil (11) are to be interpreted as symbolically representing any such sample analyte ionization means).

FIG. 1 further indicates a flow of carrier gas (4), and a controller therefore (3). It is to be noted that carrier gas flow is shown as routed to the nebulizer means (5) and to the interface means (7), as well as to multiple inlets in the inductively coupled plasma (ICP) torch system means for ionizing sample analyte(s) (9). Some embodiments of the present invention system for producing nebulized sample analyte containing solution nebulizer means (5) and interface means (7) provide for carrier gas flow entry to both thereof. See FIG. 2 carrier gas entry elements (27) and (25) for instance. However, some embodiments render carrier gas flow entry to the interface means (7) essentially impossible, (see FIG. 3 where no gap is present between the leftmost portion of the nebulizer means (5) and the hole (19) in the interface means (7) in which it is present. Carrier gas entry via carrier gas entry element (25), it can be appreciated, is provided no exit pathway and in fact said element 25 in FIG. 3 could be deleted). Reference to FIG. 4 shows that another embodiment of the present invention provides for an integrated nebulizer means and interface means, collectively identified by (5').

In use a flow of sample analyte containing solution (2) and a flow of carrier gas (4), via controller (3), are simultaneously entered to nebulizer means (5), (or (5') in FIG. 4), wherein interaction therebetween causes said sample analyte containing solution to be nebulized into a multiplicity of droplets. Said multiplicity of nebulized droplets are caused to flow into said means for receiving nebulized sample analyte containing solution (eg. a spray chamber (6)), wherein relatively large nebulized sample analyte containing droplets fall via gravity and exit said drain means (6a) and are collected in drain tank (8). Relatively small nebulized sample analyte containing droplets, however, are caused to flow into said means for ionizing sample analyte(s), (9) (11), wherein electrons are stripped from sample analyte(s), by for instance interaction with an Inductively Coupled Plasma (12). Resulting ionized sample analyte(s) are then caused to flow into said sample analysis system (13) for analysis therein.

It is to be understood that nothing in the overall system of FIG. 1 is new. The present invention is, rather, found in improvements to the nebulizer means (5) and interface means (6), for each of the cases:

a. where the nebulizer means (5) and interface means (6), are each considered as separate systems; and b. where the nebulizer means (5) and interface means (6), are considered as a functionally integrated system.

As described in the Background Section of this Disclosure, the present invention relates to systems and methods for nebulizing, and analyzing, analytes in sample analyte containing solutions. The present invention is found where in means for preventing sample delivery tube kinking and/or crushing, and/or means for preventing sample solution electrical charging and/or means for preventing sample solution "re-nebulization" effects, and/or means for preventing sample analyte carryover from one analysis procedure to a subsequent analysis procedure; during present invention method of use for introducing nebulized sample analyte into, for instance, a mass-spectrometer sample analysis system.

At this point it is beneficial to again describe known systems for nebulizing sample analyte containing sample solution termed Micro-Concentric Nebulizer Systems, (eg. MCN systems). As described in the Background Section of this Disclosure MCN systems are generally functionally similar to Direct Injection Nebulizers (DIN) systems. (MCN's) are, however, often simpler in that they comprise a primary body element with provision for simultaneous entry of both sample analyte containing sample solution and a flow of gas, and with provision for securing to a means for receiving nebulized sample analyte containing solution. A typical (MCN) system can be functionally described as comprising a centrally located sample delivery tube which is concentrically surrounded by an outer tube, such that an annular space is formed between an outer surface of said centrally located sample delivery tube and an inner surface of said outer tube. Access to said annular space is typically via access through a wall of said outer tube, such that gas entered into said annular space flows initially ninety degrees with respect to the orientation of the annular space. In use sample analyte containing solution is typically caused to flow through the sample delivery tube while carrier gas is caused to flow through said annular space. Said sample analyte containing solution and carrier gas exit adjacent to one another in a direction governed by the orientation of said sample delivery tube and said circumscribing outer tube, with the effect being that shearing forces are created on the exiting sample anlayte containing solution, which shear forces cause the sample analyte containing solution to become nebulized into a multiplicity of various diameter droplets. As described in the Background Section of this Disclosure, it has been noted that in certain applications of conventional (MCN) type sample analyte containing solution nebulizer systems, at times sample delivery tubes, (ie. tubes which carry sample analyte containing sample solution or nebulized sample analyte containing solution), become crushed at the location where they are secured in the (MCN), thereby blocking the flow path for sample analyte containing solution therethrough. This is especially true where a utility providing thin-walled capillary is utilized as sample delivery tube and ferrules are used to secure said sample delivery tube in place in an outer tube. It has also been noted that flow of sample analyte containing solution through (MCN), or similar systems can, during use, cause sample analyte containing solution therein to become electrically charged. Uncontrolled discharge of said electrical charge has been noted to induce untoward spikes in sample analysis, (eg. (MS) system), system output, thereby reducing sample analyte analysis capability. In addition, where the (MCN) is secured to a spray chamber means, it has been found that relatively large droplets of nebulized sample analyte containing solution can condense therein, and onto the end of the (MCN), (eg. a nozzle region), from which exits nebulized sample analyte containing solution in use. This can interrupt smooth flow of nebulized sample analyte containing solution, and can result in an undesirable effective "re-nebulization" of said condensed sample analyte containing solution, by gas exiting the (MCN) nozzle region. This effect is undesirable as it complicates interpretation of results provided by use of a sample analysis system into which resulting nebulized sample solution is entered. Additionally, it has been found that the presence of gaps or crevasses between an (MCN), or similar system, and an interface means into which it is mounted can cause "memory effects", where sample analyte from one sample analyte analysis procedure is retained in said gap or crevasse, and released during a subsequent sample analyte analysis procedure.

The present invention provides system means for overcoming the identified operational problems caused by:

a. sample delivery tube kinking and/or crushing where it is secured to an (MCN) or other nebulizer system;

b. the occurrence of electrostatic spike development;

c. the occurrence of sample solution "re-nebulization"; and d. the occurrence of sample analyte retention memory effect.

Figure 2:
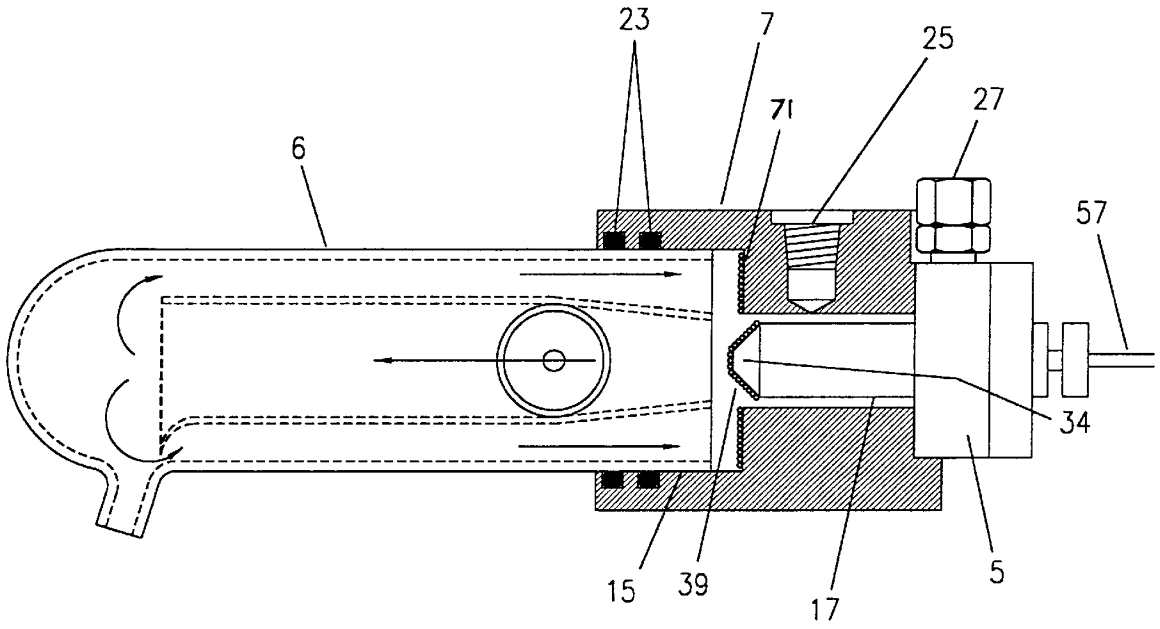
FIG. 2 shows a prior art system for producing nebulized sample analyte containing solution and for interfacing nebulized sample analyte containing solution to a sample analysis system which demonstrates sources of operational problems.

Turning attention now to FIG. 2, there is shown a prior art system for producing nebulized sample analyte containing solution and for interfacing nebulized sample analyte containing solution to a sample analysis system. Depicted is a sample delivery tube (57) secured to an (MCN) type nebulizer means (5), which nebulizer means (5) also comprises means for entering a flow of carrier gas (27). Also shown is an interface means (7) which also includes a means for entering carrier gas (25). It is to be noted that said interface means (7) has means for receiving said nebulizer means (17) at the right side thereof, said means for receiving said nebulizer means (17) being a relatively small diameter bore into the right side of said interface means (7). Said interface means (7) also has means for receiving (15) what is shown as a spray chamber (6), said means for receiving said spray chamber (6) being a relatively large bore into the left side of said interface means (7). Note that there is an essentially step change in the diameter between the right (17) and left (15) sides of said interface means (7) "through-hole", said step being identified by the numeral (71). FIG. 2 also shows "O" ring (23) securing of the spray chamber (6) into a relatively large diameter means for receiving said spray chamber (6). (Note that said means for receiving said nebulizer means

(17) at the right side of said interface means (7), and said means for receiving a means for receiving nebulized sample analyte containing solution (15), and said nebulizer means (5) and said means for receiving nebulized sample analyte containing solution (15) can be adapted with screw thread interconnection means can be and be within the scope of the present invention).

FIG. 2 further shows the left end of the nebulizer means (5) is inserted into said relatively small diameter means for receiving said nebulizer means (17). It is to be noted that a gap exists between the outer diameter surface of said left end of said nebulizer means (17) and the inner diameter surface of said means for receiving said nebulizer means (17). This gap, (or crevasse), is undesirable as in use it can retain sample analyte from one sample analysis procedure and release it during a subsequent sample analysis procedure. Note also that the far left end (39) of said nebulizer system (17), presents as a cone shaped surface. Also, when nebulized sample analyte containing solution is injected into a spray chamber (6), this cone shape has proven to be susceptible to having nebulized sample analyte containing solution which circulates in said spray chamber (6) condense, for instance, at the step change in diameter location (71) in said interface means (7), then drip thereupon, followed by flow thereof over the nebulizer system exit nozzle, which exit nozzle is identified by numeral (34). When this occurs said flowing condensate is again subjected to gas flowing out of said nozzle, in what is termed the "re-nebulization effect" herein. This effect is undesirable as it leads to instability in sample analysis system results.

Figure 3:
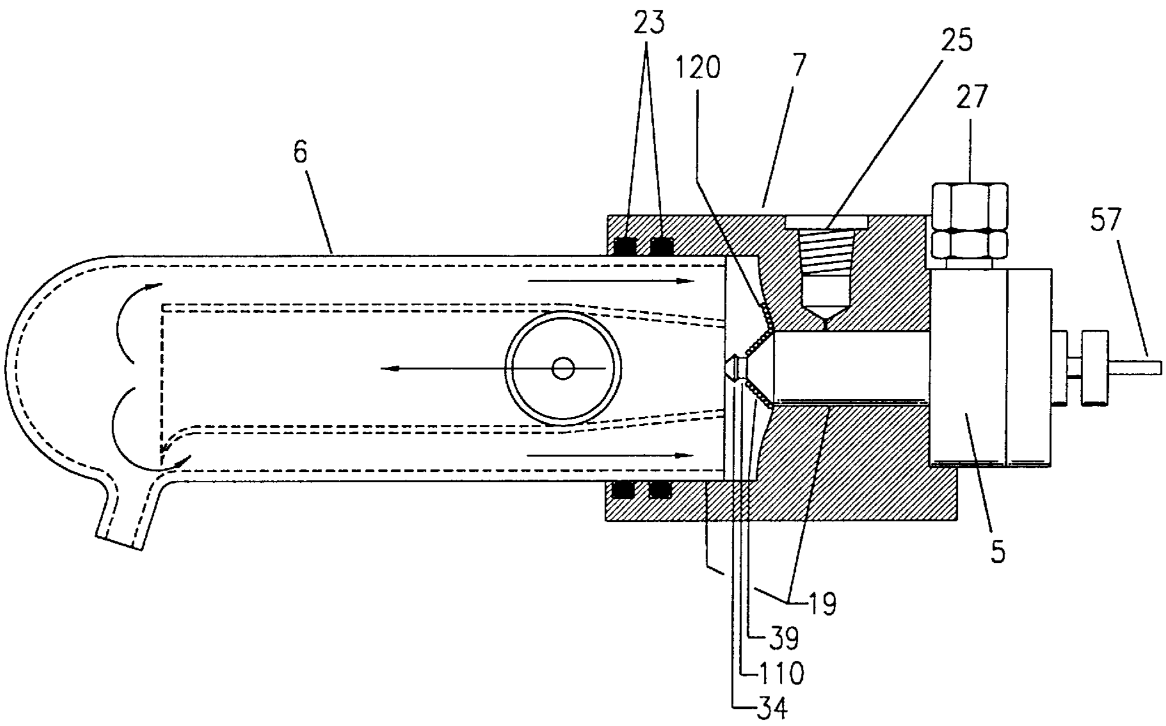
FIG. 3 shows a modified version of FIG. 2, demonstrating system improvements provided by the present invention.
Figure 4:
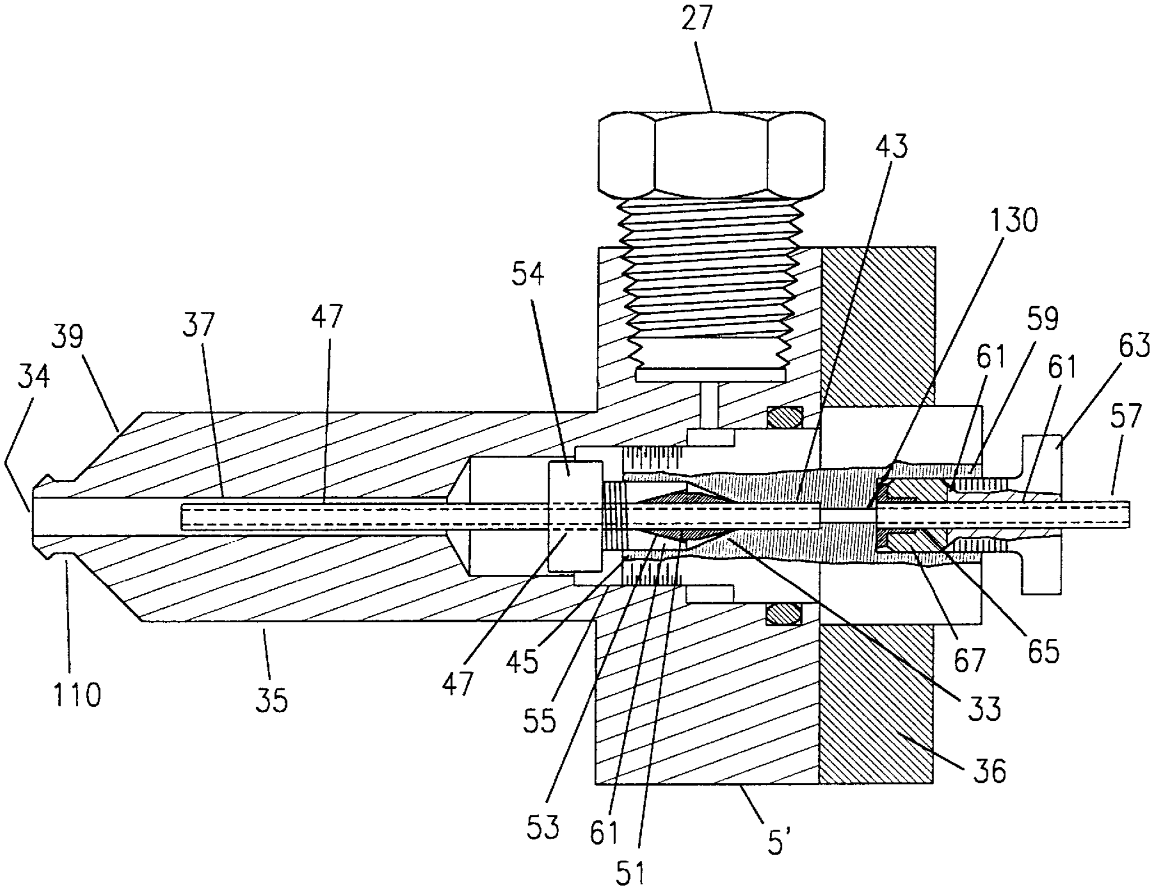
FIG. 4 shows a present invention integrated nebulizer means and interface means demonstrating improvements provided by thereby.

Continuing, turning now to FIG. 3 and comparing it to FIG. 2, provides demonstration of sample analyte containing solution nebulizing system improvements provided by the present invention. Note first that the gap between the outer diameter surface of said left end of said nebulizer means (7) and the inner diameter surface of said means for receiving said nebulizer means (17) in FIG. 2 is absent in FIG. 3. This, of course, eliminates sample analyte retention memory effects associated with said gap as described with respect to FIG. 2. Also note that the FIG. 2 region (71), as modified in FIG. 3 is no longer a step shape, but rather is a cone-like in shape (120). Further note that the region of the nebulizer means (5) to the right of the nozzle (34) is "bottle-neck" in shape, said shape being comprised of two relatively large diameter regions (34) and (39) which sandwich a relatively small diameter region (110). Note that the nozzle (34) region is placed in close proximity or against the spray chamber (6). These system attributes combine to prevent nebulized sample analyte containing solution which circulates in said spray chamber (6) and condenses, for instance, at the step change in diameter location (71) in said interface means (7), from dripping onto and flowing over the nebulizer system exit nozzle (34) at which location carrier gas exits in use. Thus, is prevented the "re-nebulization effect" which was described with respect to FIG. 2. Note that the cone-like (120) shape of the left side of the interface means (7) serves to encourage nebulized sample analyte containing solution which enters to said means for receiving nebulized sample analyte solution (6) and condenses thereat, to drip into the relatively small diameter portion (110) of the bottle-neck shaped exit means to the left of said nozzle (34), rather than over the left side of the nozzle (34) whereat it is subject to re-nebulization.

Comparison of FIGS. 2 and 3 thus show present invention system improvement means for overcoming:

the occurrence of sample solution "re-nebulization"; and the occurrence of sample analyte retention memory effect.

Turning now to FIG. 4, there is shown a present invention integrated nebulizer means and interface means (5'), with present invention system improvement means for overcoming:

sample delivery tube kinking and/or crushing where it is secured to an (MCN) or other sample analyte containing solution nebulizer system; and the occurrence of electrostatic spike development;

in addition to system improvement means for overcoming:

the occurrence of sample solution "re-nebulization"; and the occurrence of sample analyte retention memory effect.

FIG. 4 show a sample delivery tube (57) for carrying sample analyte containing sample solution into an integrated nebulizer means and interface means (5') which comprises a "through-hole" sequentially identified variously as (65), (130) and (47). Note that said sample delivery tube (57), as shown, is not continuous past the location of the barrier through-hole identified by numeral (130), and that past said barrier through-hole (130) the sample delivery tube is identified by the numeral (47). Functionally, said sample delivery tube can be described as having a tubular wall with at least one attribute selected from the group consisting of: (having at least one opening therein and having at least one discontinuity therein). In particular, the barrier through-hole region (130) could be of a sufficiently large diameter for the sample delivery tube (57) (41) to be continuous therethrough, if said sample delivery tube provides an opening therein. such that sample analyte containing solution caused to flow therein could have electrical contact to said integrated nebulizer means and interface means (5'). It will be appreciated that where said integrated nebulizer means and interface means (5') is at least partially made of an electrically conductive material, to which electrically conductive material sample analyte containing solution entered via said sample delivery tube (57) makes electrical contact in use via an opening or discontinuity therein, grounding said electrostatic spike development resulting from the flow of sample analyte containing solution during operation is substantially eliminated.

Figure 5:
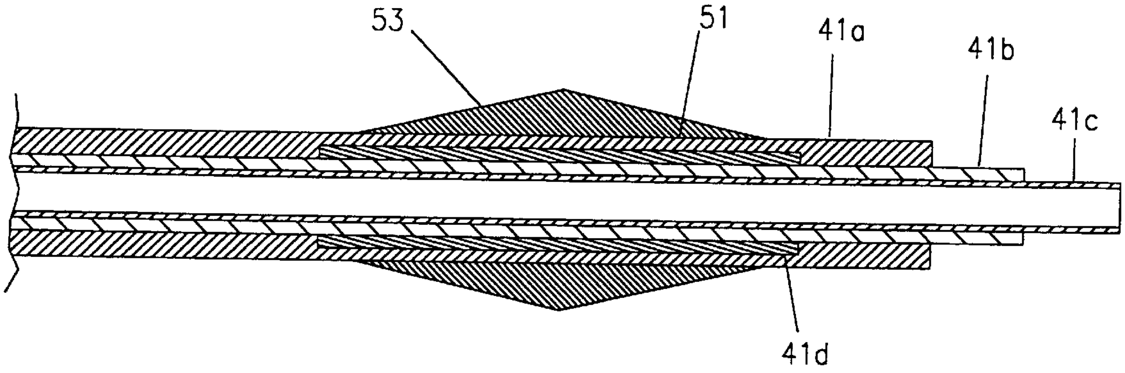
FIG. 5 demonstrates present invention system improvement for overcoming delivery tube kinking and/or crushing where it is secured in a "through-hole" of a sample analyte containing solution nebulization means by a ferrule.

Continuing, FIG. 4 shows that sample delivery tube segments (57) and (47) are secured in position in "through-hole" segments (61) and (37) respectively, by ferrules (67) and (53) respectively. At the location of ferrules (67) and/or (53), it has been found that sample delivery tube segments (57) and (47) can be crushed in use. Turning now to FIG. 5 there is shown a present invention system for preventing such crushing of sample delivery tube segment (41*c*). FIG. 5 shows that three concentric layers (41*a*), (41*b*) and (41*d*) are placed around said sample delivery tube segment (41*c*). Preferred practice is to use heat shrinkable material, (eg. teflon), for layers (41*a*) and (41*b*), and a strength providing material (eg. metal or ceramic) for layer (41*d*). Such a configuration is able to withstand securing in "through-hole" segment (37) by ferrule (53) without sample delivery tube (41*c*) being crushed. Thus the present invention can generally be recited as comprising at least two circumscribing protective concentric tubing layers around said sample delivery tube at a location thereof where said sample delivery tube is secured in said through-hole of said combination nebulizer means and interface means, said at least two protective layers serving to prevent sample delivery tube kinking and/or crushing. FIG. 5 then demonstrates sample the present invention system improvement for overcoming delivery tube kinking and/or crushing where it is secured in a "through-hole" of a sample analyte containing solution nebulization means (5) (5') by a ferrule. Identifier (51)

indicates the interface contact between heat shrinkable material (41*a*) and the strength providing material (41*d*).

FIG. 4 also demonstrates, implicitly, the providing of an annular space in which gas, entered via carrier gas flow entry element (27), can flow in use. Note that the sample delivery tube securing element (63) comprises "through-hole" (61) in which sample delivery tube segment (57) is secured and sample delivery tube securing element (63) also has present male screw threads. Additionally note that the integrated nebulizer means and interface means (5') has mating female screw threads in a means for receiving said element (63) at the right side t hereof, said means for receiving said sample delivery tube securing element (63) being a threaded bore into the right side of said integrated nebulizer means and interface means (5'). Likewise, sample delivery tube securing element (54) which comprises "through-hole" (37) in which secures sample delivery tube segment (47), has present male screw threads. Additionally note that the integrated nebulizer means and interface means (5') has mating female screw threads in a means for receiving said sample delivery tube securing element (54) at the left side thereof, said means for receiving said sample delivery tube securing element (54) being a threaded bore into the right side of said integrated nebulizer means and interface means (5'). It is to also be noted that sample delivery tube securing elements (63) and (54) provide inwardly projecting cancave tapering ends whereat contact with a sample delivery tube secufing ferruls (67) & (53), respectively, is effected. Said shape serves to provide centrally oriented forces on a contacted ferrule in use, when said sample delivery tube securing elements (63) and (54) are screwed into said integrated nebulizer means and interface means (5').

FIG. 4 also shows carrier gas flow entry element (27). In use carrier gas entered thereinto flows through the annular space inside the integrated nebulizer means and interface means (5') outside the sample delivery tube segment (47). FIG. 4 further shows that the integrated nebulizer means and interface means (5') has a "bottle-neck" shaped region (39) (110) adjacent to a nozzle (34), for the purpose of overcoming the occurrence of sample solution "re-nebulization", as described infra herein.

Figure 6:
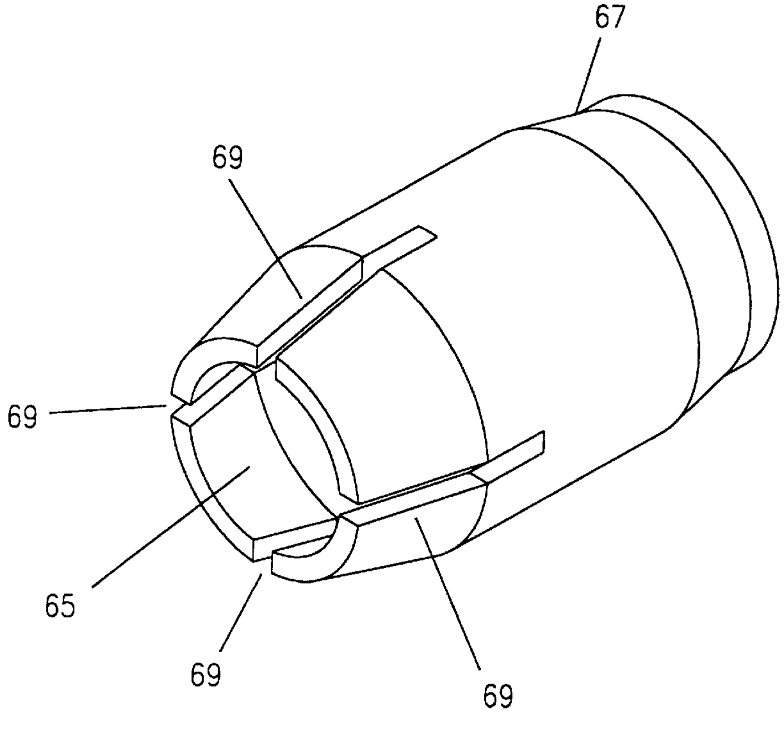
FIG. 6 shows a ferrule element such as used to secure a sample delivery tube into a "through-hole" in a system for producing nebulized sample analyte containing solution and for interfacing nebulized sample analyte containing solution to a sample analysis system.

FIG. 6 shows a ferrule (67) element such as used to secure a sample delivery tube into a "through-hole". It is to be appreciated that slits (69) provide means by which centrally directed forces can cause said ferrule to grasp a sample delivery tube caused to be present therewithin. FIG. 4 also the positioning of said slits in use in said integrated nebulizer means and interface means (5').

It should now be appreciated that the present invention provides system means solution to problems inherent in systems for producing nebulized sample analyte containing solution and for interfacing nebulized sample analyte containing solution to sample analysis systems, said problems being:

sample delivery tube kinking and/or crushing where it is secured in a (MCN), or other type, type sample analyte containing solution nebulizer system;

the occurrence of electrostatic spike development;

the occurrence of sample solution "re-nebulization"; and the occurrence of sample analyte retention memory effect.

The various Figures provide expemplary, non-limiting, examples of the implementation of present invention system means.

Having hereby disclosed the subject matter of the present invention, it should be obvious that many modifications, substitutions, and variations of the present invention are possible in view of the teachings. It is therefore to be understood that the invention may be practiced other than as specifically described, and should be limited in its breadth and scope only by the Claims.

We claim:

1. A system for use in preparing a sample analyte containing solution for introduction into a sample analysis system, comprising:

a. a sample delivery tube for carrying sample analyte containing solution;

b. a nebulizer means comprising a primary body element which contains a through-hole;

c. a means for receiving sample analyte containing solution which has been nebulized; and d. an interface means which comprises means for receiving said nebulizer means at a first side thereof and a means for receiving said means for receiving sample analyte containing solution which has been nebulized at a second side thereof;

said sample delivery tube for carrying sample analyte containing solution being secured into said through-hole of said nebulizer means, and said nebulizer means being secured into said interface means at said means for receiving said nebulizer means at a first side of said interface means, and said means for receiving sample analyte containing solution which has been nebulized being secured into said interface means at said means for receiving said means for receiving sample analyte containing solution which has been nebulized at said second side of said interface means;

such that in use sample analyte containing solution is caused to flow through said sample delivery tube and into said nebulizer means wherein it becomes nebulized, and then is caused to be injected into said means for receiving sample analyte containing solution which has been nebulized at said second side of said interface means;

in which system operational difficulties consisting of:

sample delivery tube kinking and/or crushing by means for securing it in said through-hole of said nebulizer means;

electrostatic spike development resulting from the flow of sample analyte through said sample delivery tube; and the occurrence of sample solution "re-nebulization" resulting from condensation of sample analyte containing solution which has been nebulized onto said nebulizer means;

are substantially overcome by system design which includes:

at least two circumscribing protective concentric tubing layers with no continuous annular space therebetween around said sample delivery tube at a location thereof where said sample delivery tube is secured in said through-hole of said nebulizer means, said at least two protective layers serving to prevent sample delivery tube kinking and/or crushing in use by securing effected forces;

at least one selection from the group consisting of:

an element of said nebulizer means;

said sample delivery tube; and said interface means;

with which sample analyte containing solution makes contact in use, is made of an electrically conductive material, which, in use, is connected to a charge draining "ground" so as to prevent electrostatic spike development;

an element selected from the group consisting of:

said nebulizer means; and said interface means;

serves to provide an exit means for injecting sample analyte containing solution which has been nebulized, into said means for receiving sample analyte containing solution which has been nebulized; wherein said exit means comprises a bottle-neck shape wherein a relatively small diameter portion is bounded by two relatively larger diameter portions, such that in use sample analyte containing solution which has been nebulized and which condenses in said means for receiving sample analyte containing solution which has been nebulized and, is less likely to flow over the exit means for injecting sample analyte containing solution which has been nebulized, into said means for receiving sample analyte containing solution which has been nebulized, and thereby be subject to "re-nebulization" at said exit means for injecting sample analyte containing solution which has been nebulized.

2. A system for use in preparing a sample analyte containing solution for introduction into a sample analysis system, comprising:

a. a sample delivery tube for carrying sample analyte containing solution;

b. a nebulizer means comprising a primary body element which contains a through-hole;

c. a means for receiving sample analyte containing solution which has been nebulized; and d. an interface means which comprises means for receiving said nebulizer means at a first side thereof and a means for receiving said means for receiving sample analyte containing solution which has been nebulized at a second side thereof;

said sample delivery tube for carrying sample analyte containing solution being secured into said through-hole of said nebulizer means, and said nebulizer means being secured into said interface means at said means for receiving said nebulizer means at a first side of said interface means, and said means for receiving sample analyte containing solution which has been nebulized being secured into said interface means at said means for receiving said means for receiving sample analyte containing solution which has been nebulized, at said second side of said interface means;

said sample delivery tube having circumscribing protective concentric tubing layer(s) therearound, with no continuous annular space being present between said circumscribing protective concentric tubing layer(s) and said sample delivery tube, said circumscribing protective concentric tubing layer(s) being positioned where said sample delivery tube is secured in said through-hole of said nebulizer means and serving to prevent sample delivery tube kinking and/or crushing in use, by securing effected forces;

such that in use sample analyte containing solution is caused to flow through said sample delivery tube and into said nebulizer means wherein it becomes nebulized, and then is caused to be injected into said means for receiving sample analyte containing solution which has been nebulized at said second side of said interface means;

in which system at least one operational difficulty selected from the group consisting of:

sample delivery tube kinking and/or crushing by means for securing it in said through-hole of said nebulizer means, electrostatic spike development resulting from the flow of sample analyte through said sample delivery tube, and the occurrence of sample solution "re-nebulization" resulting from condensation of sample analyte containing solution which has been nebulized onto said nebulizer means;

is/are substantially overcome by system design.

3. A system for use in preparing a sample analyte containing solution for introduction into a sample analysis system as in claim 2, in which there are three circumscribing protective concentric tubing layers with no continuous annular space therebetween, the first and third thereof being made of at least one material selected from the group consisting of:

a fluorocarbon,

PTFE;

PFA; and a polyimide;

the middlemost thereof being made of at least one material selected from the group consisting of:

a metal;

a ceramic;

stainless steel;

a rigid plastic; and

PEEK;

and in which said sample delivery tube is secured in said through-hole of said nebulizer means by a ferrule.

4. A system for use in preparing a sample analyte containing solution for introduction into a sample analysis system as in claim 2, in which at least one selection from the group consisting of:

an element of said nebulizer means; and said sample delivery tube;

with which sample analyte containing solution makes contact in use, is made of an electrically conductive material, which is connected to charge draining "ground" so as to prevent electrostatic spike development.

5. A system for use in preparing a sample analyte containing solution for introduction into a sample analysis system as in claim 4, in which an element of said nebulizer means is made of an electrically conductive material, said sample delivery tube being other than totally confining of sample analyte containing solution entered thereinto such that said entered sample analyte containing solution is provided access to said electrically conductive material, to the end that sample analyte containing solution caused to enter said nebulizer means, in use, makes direct contact electrical with said electrically conductive material.

6. A system for use in preparing a sample analyte containing solution for introduction into a sample analysis system as in claim 5, in which the electrically conductive material is graphite impregnated PEEK.

7. A system for use in preparing a sample analyte containing solution for introduction into a sample analysis system as in claim 2, in which an element selected from the group consisting of:

said nebulizer means; and said interface means, serves to provide an exit means for injecting sample analyte containing solution which has been nebulized, into said means for receiving sample analyte containing solution which has been nebulized; wherein said exit means comprises a bottle-neck shape wherein a relatively small diameter portion is bounded by two relatively larger diameter portions, such that in use sample analyte containing solution which has been nebulized and which condenses in said means for receiving sample analyte containing solution which has been nebulized, is less likely to flow over the exit means for injecting sample analyte containing solution which has been nebulized, into said means for receiving sample analyte containing solution which has been nebulized, and thereby be subject to "re-nebulization" at said exit means for injecting sample analyte containing solution which has been nebulized.

8. A system for use in preparing a sample analyte containing solution for introduction into a sample analysis system, comprising:

a. a sample delivery tube for carrying sample analyte containing solution;

b. a nebulizer means comprising a primary body element which contains a through-hole;

c. a means for receiving sample analyte containing solution which has been nebulized; and d. an interface means which comprises means for receiving said nebulizer means at a first side thereof and a means for receiving said means for receiving sample analyte containing solution which has been nebulized at a second side thereof;

said sample delivery tube for carrying sample analyte containing solution being secured into said through-hole of said nebulizer means, and said nebulizer means being secured into said interface means at said means for receiving said nebulizer means at a first side of said interface means, and said means for receiving sample analyte containing solution which has been nebulized being secured into said interface means at said means for receiving said means for receiving sample analyte containing solution which has been nebulized at said second side of said interface means;

such that in use sample analyte containing solution is caused to flow through said sample delivery tube and into said nebulizer means wherein it becomes nebulized, and then is caused to be injected into said means for receiving sample analyte containing solution which has been nebulized at said second side of said interface means;

in which at least one system operational difficulty selected from the group consisting of consisting of:

sample delivery tube kinking and/or crushing by means for securing it in said through-hole of said nebulizer means;

electrostatic spike development resulting from the flow of sample analyte through said sample delivery tube; and the occurrence of sample solution "re-nebulization" resulting from condensation of sample analyte containing solution which has been nebulized onto said nebulizer means;

is/are substantially overcome by system design which includes at least one selection from the group consisting of:

said system for use in preparing a sample analyte containing solution for introduction into a sample analysis system further comprises at least two circumscribing protective concentric tubing layers around said sample delivery tube at a location thereof where said sample delivery tube is secured in said through-hole of said nebulizer means, said at least two protective layers having no continuous annular space therebetween, and, in use, serving to prevent sample delivery tube kinking and/or crushing in use by securing effected forces;

b. said system for use in preparing a sample analyte containing solution for introduction into a sample analysis system, further comprises at least two circumscribing protective concentric tubing layers around said sample delivery tube at a location thereof where said sample delivery tube is secured in said through-hole of said nebulizer means, said at least two protective layers having no continuous annular space therebetween, and, in use, serving to prevent sample delivery tube kinking and/or crushing in use by securing effected forces, in which one circumscribing protective concentric tubing layer is made of at least one material selected from the group consisting of:

a fluorocarbon;

PTFE;

PFA;

a polyimide;

a metal;

a ceramic;

stainless steel;

a rigid plastic; and

PEEK; and in which said sample delivery tube is secured in said through-hole of said nebulizer means by a ferrule;

c. said system for use in preparing a sample analyte containing solution for introduction into a sample analysis system, in which at least one selection from the group consisting of:

an element of said nebulizer means; and said sample delivery tube;

with which sample analyte containing solution makes contact in use, is made of an electrically conductive material, which, in use, is connected to charge draining "ground" so as to prevent electrostatic spike development;

d. said system for use in preparing a sample analyte containing solution for introduction into a sample analysis system, in which an element of said nebulizer means is made of an electrically conductive material and in which said sample delivery tube is other than totally confining of sample analyte containing solution entered thereinto, to the end that sample analyte containing solution caused to enter said nebulizer means, in use, makes direct contact electrical with said electrically conductive material;

e. said system for use in preparing a sample analyte containing solution for introduction into a sample analysis system, in which an element selected from the group consisting of:

said nebulizer means; and said interface means;

serves to provide an exit means for injecting sample analyte containing solution which has been nebulized, into said means for receiving sample analyte containing solution which has been nebulized; wherein said exit means comprises a bottle-neck shape wherein a relatively small diameter portion is bounded by two relatively larger diameter portions, such that in use sample analyte containing solution which has been nebulized and which condenses in said means for receiving sample analyte containing solution which has been nebulized, is less likely to flow over the exit means for injecting sample analyte containing solution which has been nebulized, into said means for receiving sample analyte containing solution which has been nebulized, and thereby be subjected to "re-nebulization" at said exit means for injecting sample analyte containing solution which has been nebulized.

9. A system for use in preparing a sample analyte containing solution for introduction into a sample analysis system, comprising:

a. a sample delivery tube for carrying sample analyte containing solution, said sample delivery tube having a tubular wall with at least one attribute selected from the group consisting of:

having at least one opening therein;and having at least one discontinuity therein;

at a location other than at an end of said sample delivery tube at which sample analyte containing solution is ejected and directly thereafter nebulized by interaction with a flow of carrier gas in use;

b. a integrated nebulizer means and interface means comprising a through-hole and means for receiving a means for receiving sample analyte containing solution which has been nebulized;

such that said sample delivery tube for carrying sample analyte containing solution is secured into said through-hole of said combination nebulizer means and interface means;

said integrated nebulizer means and interface means being at least partially made of an electrically conductive material to which electrically conductive material sample analyte containing solution entered via said sample delivery tube makes electrical contact in use via said opening or discontinuity therein, to the end that electrostatic spike development resulting from the flow of sample analyte containing solution during operation is substantially eliminated;

which system for use in preparing a sample analyte containing solution for introduction into a sample analysis system further comprises at least two circumscribing protective concentric tubing layers having no continuous annular space therebetween around said sample delivery tube at a location thereof where said sample delivery tube is secured in said through-hole of said integrated nebulizer means and interface means, said at least two protective layers serving to prevent sample delivery tube kinking and/or crushing.

10. A system for use in preparing a sample analyte containing solution for introduction into a sample analysis system as in claim 9, in which sample delivery tube securing effected forces, are developed by ferrule (s) present in said through-hole.

11. A system for use in preparing a sample analyte containing solution for introduction into a sample analysis system as in claim 1, which further sequentially comprises an inductively coupled plasma (ICP) or functionally equivalent sample analyte ionization system functionally attached to said means for receiving sample analyte containing solution which has been nebulized, wherein said inductively coupled plasma (ICP) or functionally equivalent sample analyte ionization system, ionization of sample analyte(s) occurs in use to the end that said mass spectrometer (MS) system can be applied to the detection, and analysis, of sample analyte(s) present therein.

12. A system for use in preparing a sample analyte containing solution for introduction into a sample analysis system as in claim 2, which further sequentially comprises an inductively coupled plasma (ICP) or functionally equivalent sample analyte ionization system functionally attached to said means for receiving sample analyte containing solution which has been nebulized, wherein said inductively coupled plasma (ICP) or functionally equivalent sample analyte ionization system, ionization of sample analyte(s) occurs in use to the end that said mass spectrometer (MS) system can be applied to the detection, and analysis, of sample analyte(s) present therein.

13. A system for use in preparing a sample analyte containing solution for introduction into a sample analysis system as in claim 9, which further sequentially comprises an inductively coupled plasma (ICP) or functionally equivalent sample analyte ionization system functionally attached to said means for receiving sample analyte containing solution which has been nebulized, wherein said inductively coupled plasma (ICP) or functionally equivalent sample analyte ionization system, ionization of sample analyte(s) occurs in use to the end that said mass spectrometer (MS) system can be applied to the detection, and analysis, of sample analyte(s) present therein.

14. A system for use in preparing a sample analyte containing solution for introduction into a sample analysis system as in claim 1, which further comprises a means for entering a sample analyte containing solution nebulizing flow of carrier gas in at least one selection from the group consisting of:

a. said nebulizer means; and b. said interface means;

and which also further comprises a drain means in said means for receiving sample analyte containing solution which has been nebulized.

15. A system for use in preparing a sample analyte containing solution for introduction into a sample analysis system as in claim 2, which further comprises a means for entering a sample analyte containing solution nebulizing flow of carrier gas in at least one selection from the group consisting of:

a. said nebulizer means; and b. said interface means;

and which also further comprises a drain means in said means for receiving sample analyte containing solution which has been nebulized.

16. A system for use in preparing a sample analyte containing solution for introduction into a sample analysis system as in claim 9, which further comprises a means for entering a sample analyte containing solution nebulizing flow of carrier gas in at least one selection from the group consisting of:

a. said nebulizer means; and b. said interface means;

in said integrated nebulizer means and interface means.

17. A system for use in preparing a sample analyte containing solution for introduction into a sample analysis system as in claim 9, which further comprises at least one means for entering a sample analyte containing solution nebulizing flow of carrier gas in said integrated nebulizer means and said interface means, and which also further comprises a means for receiving sample analyte containing solution which has been nebulized functionally attached to said integrated nebulizer means and interface means, said means for receiving sample analyte containing solution which has been nebulized including a drain means.

18. A system for use in preparing a sample analyte containing solution for introduction into a sample analysis system as in claim 1, in which said interface means for receiving said nebulizer means at a first side thereof and means for receiving said means for receiving sample analyte containing solution which has been nebulized at a second side thereof are each an essentially tubular threaded female hole, and said nebulizer means primary body element and means for receiving sample analyte containing solution which has been nebulized each have complimentary mating threaded male shafts; such that in use said nebulizer means primary body element is affixed to said interface means for receiving said nebulizer means at said first side thereof by being screwed thereinto, and such that said means for receiving sample analyte containing solution which has been nebulized is affixed to said interface means for receiving said nebulizer means at said second side thereof by being screwed thereinto.

19. A system for use in preparing a sample analyte containing solution for introduction into a sample analysis system, comprising:

a. a sample delivery tube for carrying sample analyte containing solution;

b. a nebulizer means comprising a primary body element which contains a through-hole;

c. a means for receiving sample analyte containing solution which has been nebulized; and d. an interface means which comprises means for receiving said nebulizer means at a first side thereof and a means for receiving said means for receiving sample analyte containing solution which has been nebulized at a second side thereof;

said sample delivery tube for carrying sample analyte containing solution being secured into said through-hole of said nebulizer means, and said nebulizer means being secured into said interface means at said means for receiving said nebulizer means at a first side of said interface means, and said means for receiving sample analyte containing solution which has been nebulized being secured into said interface means at said means for receiving said means for receiving sample analyte containing solution which has been nebulized, at said second side of said interface means;

said sample delivery tube having circumscribing protective concentric tubing layer(s) therearound, with no continuous annular space being present between said circumscribing protective concentric tubing layer(s) and said sample delivery tube, said circumscribing protective concentric tubing layer(s) being positioned where said sample delivery tube is secured in said through-hole of said nebulizer means and serving to prevent sample delivery tube kinking and/or crushing in use, by securing effected forces;

such that in use sample analyte containing solution is caused to flow through said sample delivery tube and into said nebulizer means wherein it becomes nebulized, and then is caused to be injected into said means for receiving sample analyte containing solution which has been nebulized at said second side of said interface means;

in which system at least one operational difficulty selected from the group consisting of:

sample delivery tube kinking and/or crushing by means for securing it in said through-hole of said nebulizer means, electrostatic spike development resulting from the flow of sample analyte through said sample delivery tube, and the occurrence of sample solution "re-nebulization" resulting from condensation of sample analyte containing solution which has been nebulized onto said nebulizer means;

is/are substantially overcome by system design;

in which interface means for receiving said nebulizer means at a first side thereof and means for receiving said means for receiving sample analyte containing solution which has been nebulized at a second side thereof are each an essentially tubular threaded female hole, and said nebulizer means primary body element and means for receiving sample analyte containing solution which has been nebulized each have complimentary mating threaded male shafts; such that in use said nebulizer means primary body element is affixed to said interface means for receiving said nebulizer means at said first side thereof by being screwed thereinto, and such that said means for receiving sample analyte containing solution which has been nebulized is affixed to said interface means for receiving said nebulizer means at said second side thereof by being screwed thereinto.

20. A system for use in preparing a sample analyte containing solution for introduction into a sample analysis system as in claim 9, in which said integrated nebulizer means and interface means has a threaded female hole therein for receiving said means for receiving sample analyte containing solution which has been nebulized, and said means for receiving sample analyte containing solution which has been nebulized has a complimentary mating threaded male shaft; such that in use said means for receiving sample analyte containing solution which has been nebulized is affixed to said integrated nebulizer means and interface means for receiving said nebulizer means by being screwed thereinto.

21. A sample introduction system comprising:

a nebulizer means comprising means for simultaneously introducing sample analyte containing solution, and a flow of carrier gas, to the end that said sample analyte containing solution is nebulized into droplets of varying sizes;

a spray chamber means, for receiving nebulized sample analyte containing solution, and being capable of condensing relatively large diameter droplets and expelling them therefrom;

an interface means having a through-hole comprising a first diameter side and a second diameter side;

a sample delivery tube for use in providing sample analyte containing solution into said nebulizer means, said sample delivery tube being secured in said nebulizer means by ferrule means;

the through-hole of said interface means, at each of said first and second diameter sides thereof, being a threaded, essentially tubular shaped female hole, and said nebulizer means and said spray chamber means each having complimentary mating threaded male shafts; such that in use said nebulizer means is affixed to said interface means at said first side thereof by being screwed thereinto, and such that said spray chamber means is affixed to said interface means for receiving said nebulizer means at said second side thereof by being screwed thereinto.

22. A sample introduction system as in claim 21, which further comprises at least two circumscribing protective concentric tubing layers having no continuous annular space therebetween around said sample delivery tube at the location thereof where said sample delivery tube is secured in said nebulizer means by said ferrule means, said at least two protective layers serving to prevent sample delivery tube kinking and/or crushing.

23. A sample introduction system as in claim 21, in which an element selected from the group consisting of:

said nebulizer means; and said interface means;

serves to provide an exit means for injecting sample analyte containing solution which has been nebulized by said nebulizer means, into said spray-chamber means, said exit means having a bottle-neck shape wherein a relatively small diameter portion is bounded by two relatively larger diameter portions, a portion of said means for injecting sample analyte containing solution which has been nebulized by said nebulizer means beyond said bottle-neck shape being a nozzle, such that in use nebulized sample analyte containing solution which enters to and condenses in said spray-chamber means, is less likely to flow over the nozzle region of said exit means for injecting sample analyte containing solution into said spray-chamber means, and is thereby less likely to be subject to "re-nebulization" at said nozzle.

24. A sample introduction system as in claim 21, in which said sample delivery tube is optionally discontinuous within said said nebulizer means, and wherein at least one selection from the group consisting of:

an element of said nebulizer means; and said sample delivery tube;

with which sample analyte containing solution makes contact in use, is made of an electrically conductive material, which, in use, is connected to a charge draining "ground" so as to prevent electrostatic spike development.

25. A sample introduction system as in claim 21, in which said nebulizer means is affixed to said interface means at said first side thereof by being screwed thereinto in a manner such that no sample analyte containing solution retaining gaps are present between said nebulizer means said interface means.

26. A sample introduction system as in claim 21, in which said interface means through-hole at said first side thereof and at said second side thereof communicate via a relatively small diameter hole therebetween, with the transition between said relatively small diameter hole and said through-hole at said second side of said interface means being essentially cone shaped.

27. A system for use in preparing a sample analyte containing solution for introduction into a sample analysis system, comprising:

a. an interface means for receiving a first element at a first side thereof and means for receiving a second element at a second side thereof, said means for receiving a first element and means for receiving a second element being separated by a barrier in said interface means which has a barrier through-hole therein which interconnects said means for receiving a first element at said first side thereof and means for receiving a second element at said second side thereof, each of said means for receiving a first element and means for receiving a second element being an essentially tubular threaded female hole;

said first element and second element each comprising a threaded male shaft; such that in use said first element is affixed to said interface receiving means by being screwed thereinto, and such that said second element is affixed to said interface means at said second side thereof by being screwed thereinto;

b. each of said first and second elements having through-holes into each of which is secured a sample delivery tube segment, each of said first and second element through-holes having an into-the-element directed tapering concave shape region near ends thereof which become positioned adjacent to said barrier when said first and second elements are screwed into said interface means, said tapering shape region shape being appropriate for receiving a ferrule which is slide over the sample delivery tube segment present in the element which affixes to the respective means for receiving an element adjacent to said tapering shape region;

c. said barrier, on at least one side thereof, having a tapering shape region near said barrier through-hole, said tapering shape region being appropriate for receiving a ferrule which slides over the sample delivery tube segment present in the first and/or second element which affixes to said interface means at said at least one side of said barrier;

d. such that when each said first and second elements have sample delivery tube segments present in through-holes therein, and when ferrules are slid over the sample delivery tube segments at ends thereof which become positioned adjacent to said barrier in use, and when said first and second elements are screwed into said interface means, said ferrules are partially collapsed by adjacent tapering shape regions in said first and second elements, thereby securing said sample delivery tube segments;

e. said interface means further comprising, at one side thereof, a sample delivery tube segment containing exit means which, in use, receives sample analyte containing solution through said barrier through-hole and adjacent sample delivery tube segment, said exit means having a bottle-neck shape wherein a relatively small diameter portion is bounded by two relatively larger diameter portions, a portion of said interface means beyond said bottle-neck shape being a nozzle region;

f. said interface means further comprising means for entering a sample analyte containing solution nebulizing flow of carrier gas into an annular space formed around the outer surface of the sample delivery tube segment which provides sample analyte containing solution to said nozzle region, such that in use gas and sample analyte containing solution simultaneously exit at said nozzle region and interact to the end that said sample analyte containing solution becomes nebulized;

the purpose of said bottle-neck shape being to cause sample analyte containing solution which becomes nebulized and exits said nozzle region as nebulized sample analyte containing solution and then condenses, to be less likely to flow over the nozzle region of said exit means and as a result become "re-nebulized" by carrier gas exiting at said nozzle, but rather is more likely to flow into the relatively small diameter portion of the bottle-neck region;

such that in use sample analyte containing solution is entered to the sample delivery tube segment present at the side of the interface means which does not have the exit means, such that said sample analyte containing solution flows through said barrier through-hole, into the sample delivery tube segment at the side of the interface means which has the exit means, and such that a flow of carrier gas is entered to said means for entering a sample analyte containing solution nebulizing flow of carrier gas;

the result being that entered sample analyte containing solution is nebulized into a multiplicity of nebulized droplets which are ejected from said nozzle region.

28. A system for use in preparing a sample analyte containing solution for introduction into a sample analysis system, comprising:

a. a sample delivery tube for carrying sample analyte containing solution;

b. a nebulizer means comprising a primary body element which contains a through-hole;

c. a means for receiving sample analyte containing solution which has been nebulized; and d. an interface means which comprises means for receiving said nebulizer means at a first side thereof and a means for receiving said means for receiving sample analyte containing solution which has been nebulized at a second side thereof;

said sample delivery tube for carrying sample analyte containing solution being secured into said through-hole of said nebulizer means, and said nebulizer means being secured into said interface means at said means for receiving said nebulizer means at a first side of said interface means, and said means for receiving sample analyte containing solution which has been nebulized being secured into said interface means at said means for receiving said means for receiving sample analyte containing solution which has been nebulized at said second side of said interface means;

such that in use sample analyte containing solution is caused to flow through said sample delivery tube and into said nebulizer means wherein it becomes nebulized, and then is caused to be injected into said means for receiving sample analyte containing solution which has been nebulized, at said second side of said interface means;

said system further requiring that at least one selection from the group consisting of:

said nebulizer means; and said interface means;

serves to provide an exit means for injecting sample analyte containing solution which has been nebulized, into said means for receiving sample analyte containing solution which has been nebulized; wherein said exit means comprises a bottle-neck shape wherein a relatively small diameter portion is bounded by two relatively larger diameter portions, such that in use sample analyte containing solution which has been nebulized and which condenses in said means for receiving sample analyte containing solution which has been nebulized, is less likely to flow over the exit means for injecting sample analyte containing solution which has been nebulized, into said means for receiving sample analyte containing solution which has been nebulized, and thereby be subject to "re-nebulization" at said exit means for injecting sample analyte containing solution which has been nebulized;

in which system at least one operational difficulty selected from the group consisting of:

sample delivery tube kinking and/or crushing by means for securing it in said through-hole of said nebulizer means, electrostatic spike development resulting from the flow of sample analyte through said sample delivery tube, and the occurrence of sample solution "re-nebulization" resulting from condensation of sample analyte containing solution which has been nebulized onto said nebulizer means;

is/are substantially overcome by system design.

* * * * *